(12) United States Patent
Schumacher et al.

(10) Patent No.: US 6,175,977 B1
(45) Date of Patent: Jan. 23, 2001

(54) SYSTEM FOR TRANSPORTING A SICK OR INJURED PERSON TO A MEDICAL FACILITY

(75) Inventors: Markus Schumacher, Buxtehude; Andrew Muin, Harsefeld, both of (DE)

(73) Assignee: DaimlerChrysler Aerospace Airbus GmbH, Hamburg (DE)

( * ) Notice: Under 35 U.S.C. 154(b), the term of this patent shall be extended for 0 days.

(21) Appl. No.: 09/309,904

(22) Filed: May 11, 1999

(30) Foreign Application Priority Data

May 14, 1998 (DE) .............................................. 198 21 692

(51) Int. Cl.$^7$ ................................ A61G 1/00; A61G 7/00; A61G 7/05; A47B 23/02; A45F 3/00
(52) U.S. Cl. ................................ 5/626; 5/503.1; 5/507.1; 5/658; 128/845; 224/153; 224/584; 312/209
(58) Field of Search .................... 5/658, 503.1, 507.1, 5/625, 626, 600; 296/20; 128/845, 846, 870; 248/349.1; 224/153, 584, 585; 312/209

(56) References Cited

U.S. PATENT DOCUMENTS

| | | | |
|---|---|---|---|
| 2,678,792 | * | 5/1954 | Gallion et al. ........................ 5/503.1 |
| 2,696,963 | * | 12/1954 | Shepherd .............................. 5/503.1 |
| 3,427,668 | * | 2/1969 | McManus, Jr. ....................... 5/503.1 |
| 3,761,968 | * | 10/1973 | Besler ...................................... 5/626 |
| 3,954,244 | * | 5/1976 | Gopstein ............................ 248/349.1 |
| 4,223,819 | * | 9/1980 | Wright ................................. 226/153 |
| 4,352,991 | * | 10/1982 | Kaufman ................................ 296/20 |
| 4,557,453 | * | 12/1985 | McCloskey ............................ 5/507.1 |
| 4,691,397 | * | 9/1987 | Netzer .................................... 5/507.1 |
| 4,747,172 | * | 5/1988 | Hobol et al. .......................... 5/507.1 |
| 4,783,109 | * | 11/1988 | Bucalo .................................. 5/507.1 |
| 5,573,154 | * | 11/1996 | Tietze .................................... 224/153 |
| 5,634,576 | * | 6/1997 | Arbel .................................... 224/153 |
| 5,860,176 | * | 1/1999 | Norberg ................................... 5/628 |
| 5,918,331 | * | 7/1999 | Hall et al. ............................... 5/626 |

FOREIGN PATENT DOCUMENTS

| | | |
|---|---|---|
| 9006453 U | 11/1990 | (DE) . |
| WO96/08218 | 3/1996 | (WO) . |

* cited by examiner

*Primary Examiner*—Alexander Grosz
(74) *Attorney, Agent, or Firm*—W. F. Fasse; W. G. Fasse

(57) ABSTRACT

A system for transporting an ill or injured patient includes a stretcher in combination with a plurality of medical care modules that respectively include medical devices such as an infusion pump, an oxygen supply device, a defibrillator, an EKG unit, or the like, and medical and first aid supplies such as bandages, splints, IV supplies, drugs, medical instruments, and the like. The stretcher includes a frame and a patient support surface, as well as module bays provided under the frame or a module carrier removably mounted on the frame. The several medical care modules each have the same dimensions and configuration so that they are modularly interchangeable to be received in any one of the module bays or on the module carrier. When the medical care modules are slidingly pushed into the module bays, electrical contacts are engaged to connect the modules with an electrical power supply and a data transfer bus, through the stretcher.

30 Claims, 4 Drawing Sheets

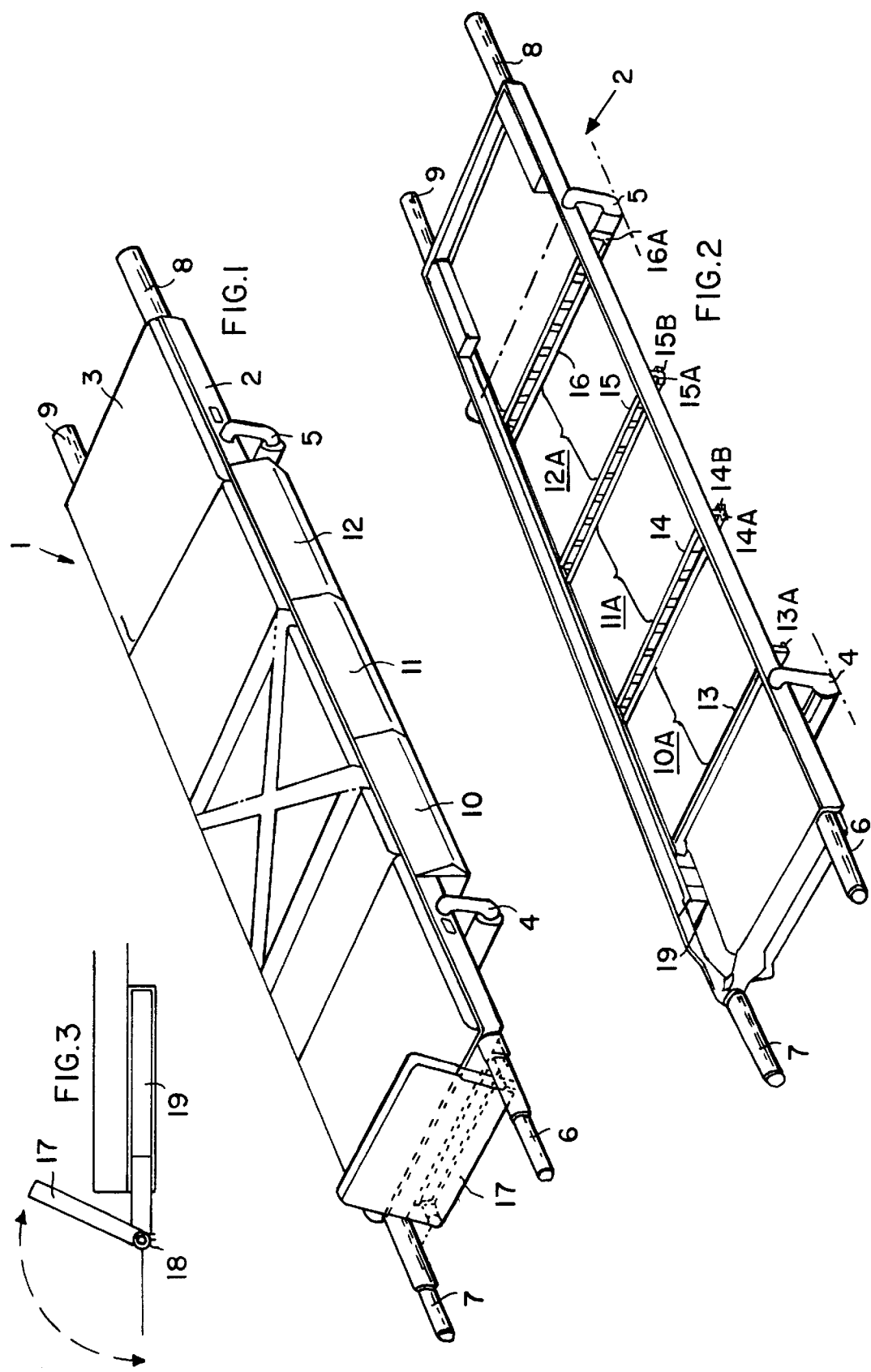

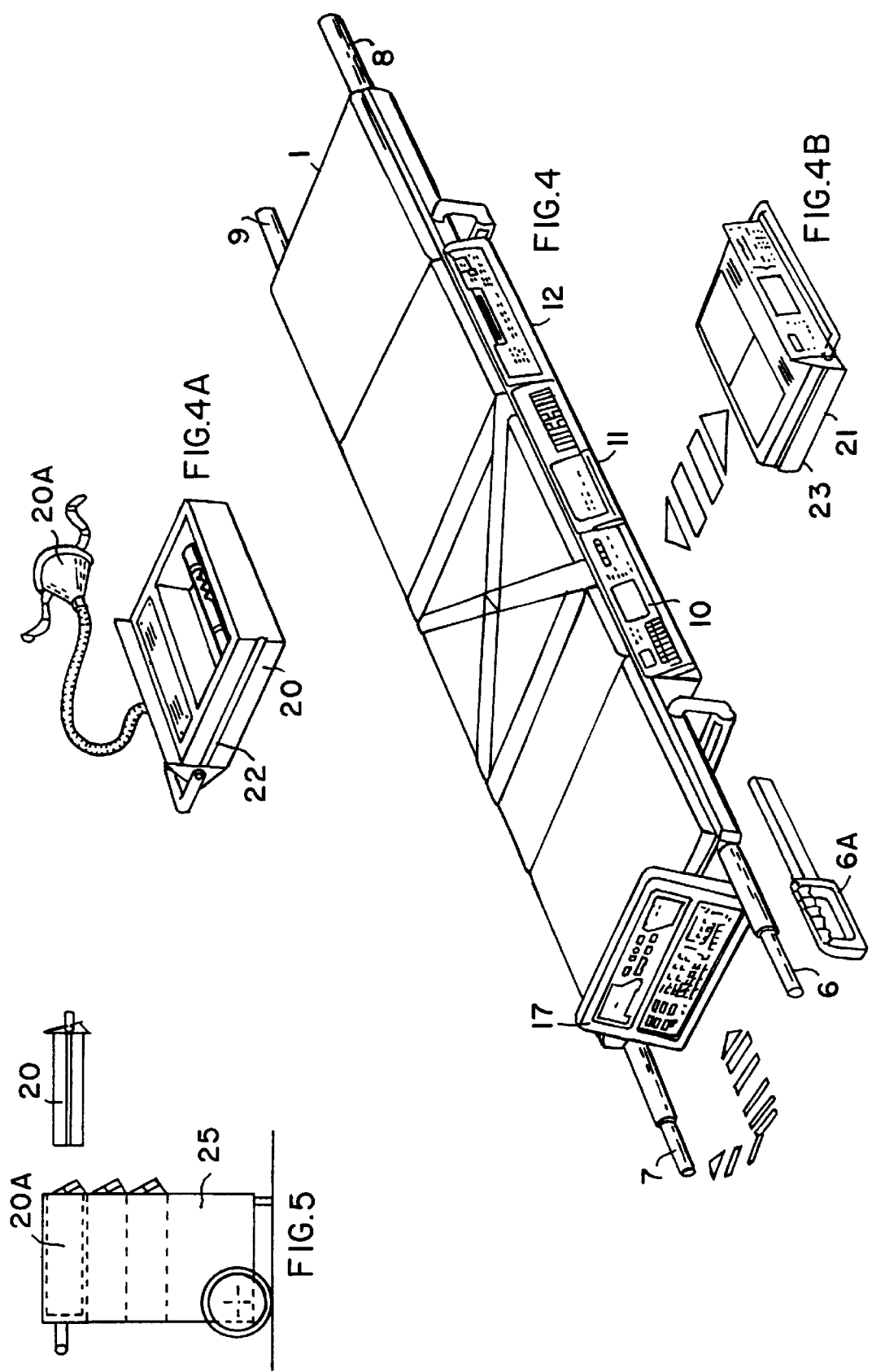

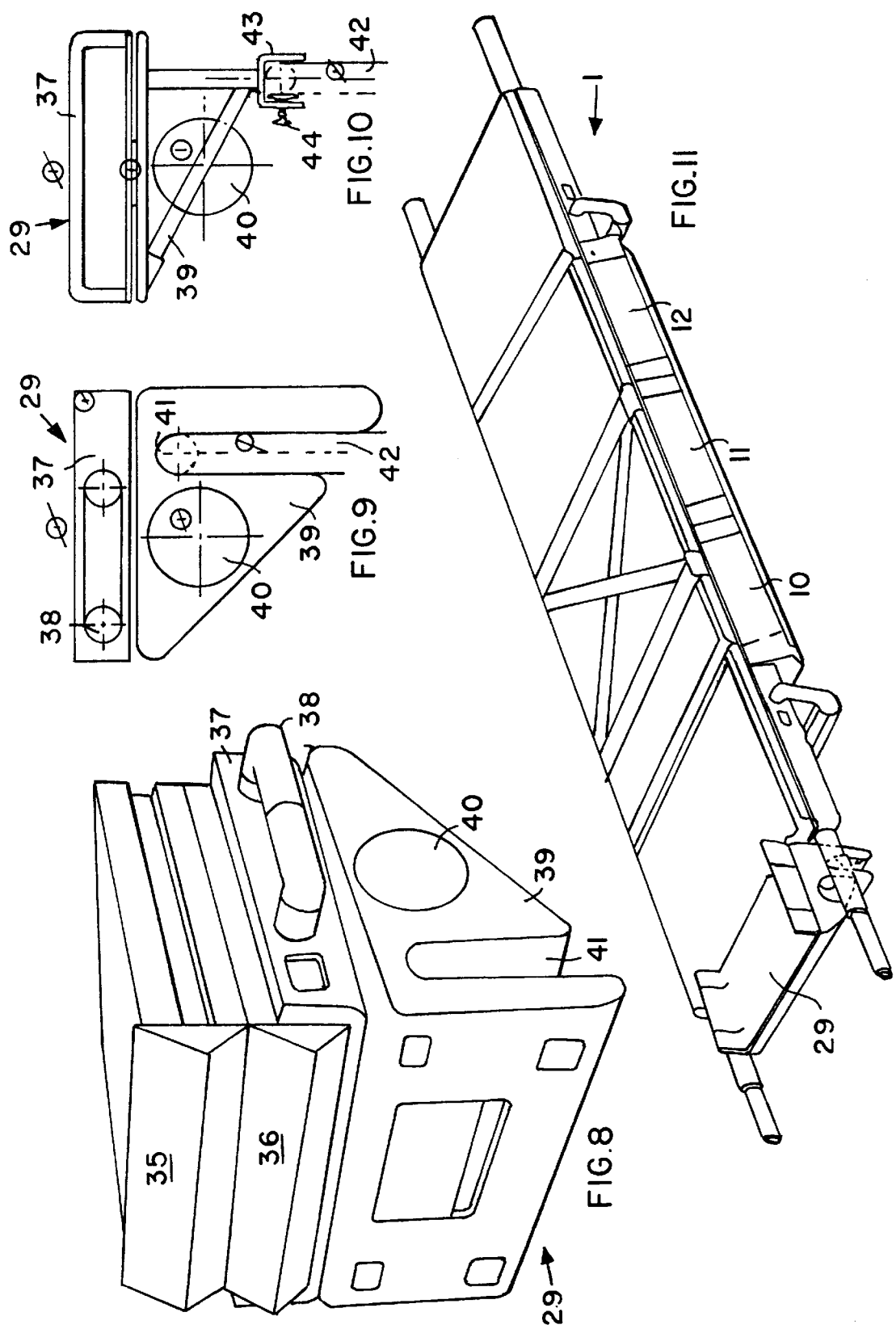

SYSTEM FOR TRANSPORTING A SICK OR INJURED PERSON TO A MEDICAL FACILITY

PRIORITY CLAIM

This application is based on and claims the priority under 35 U.S.C. §119 of German Patent Application 198 21 692.0, filed on May 14, 1998, the entire disclosure of which is incorporated herein by reference.

FIELD OF THE INVENTION

The invention relates to a system for transporting a sick or injured person between a location at which the person became ill or injured and a medical facility, essentially including a stretcher for carrying the patient as well as medical care devices such as an infusion pump, an oxygen supply device, and a defibrillator, for example.

BACKGROUND INFORMATION

According to the current state of the art and current practice, a person who is sick or injured in an accident for example, generally called a "patient" herein, is typically transported the location at which he became ill or injured to a hospital or other medical facility by emergency medical technicians (EMTs) or other medical or rescue personnel, in a transport vehicle such as an ambulance or medical evacuation aircraft. The patient is carried and supported on a stretcher from the location of illness or injury into the ambulance, during transport in the ambulance, and then from the ambulance into the hospital.

During such transportation of the patient, and especially a seriously ill or seriously injured patient, various first aid and emergency medical response procedures are carried out and administered to the patient. For this purpose, it is often necessary for the EMTs or other personnel to carry along various medical devices such as an infusion pump, an oxygen supply device, a defibrillator, an electrocardiograph (EKG), intravenous (IV) equipment and the like, as well as medical supplies. Conventionally, these medical accessories must be carried by an additional attendant, or in many cases, these devices are simply laid on the stretcher next to the patient or directly onto the body of the patient. Moreover, due to the lack of portability and the limitations of the medical personnel in carrying all of the possibly needed medical accessories, certain medical devices or supplies will not even be carried along, and thus will not be utilized for treating the patient during transport from the location of injury or accident to the medical facility.

The above mentioned situations, of course, detract from the quality of the first aid and emergency medical response procedures being administered to the patient. Moreover, it is difficult or impossible to continuously administer the necessary treatments or to carry out the necessary assessments without interruption from the time the patient is first picked up on the stretcher until the patient is transferred to a hospital bed or the like.

SUMMARY OF THE INVENTION

In view of the above, it is an object of the invention to provide a system for transporting an ill or injured patient that meets the needs of a modern emergency medical response and rescue service and makes it possible to continuously provide the necessary medical treatment and assessment without interruption from the time of picking up the patient at the location of illness or injury until the time of transferring the patient to the hospital or other end destination. It is particularly an object of the invention to provide a stretcher that provides means for storing and carrying along any necessary medical devices, equipment and supplies, without requiring the medical personnel to individually carry the several devices or to place the devices loosely on top of the stretcher or the patient. The invention further aims to avoid or overcome the disadvantages of the prior art, and to achieve additional advantages, as apparent from the present specification.

The above objects have been achieved in a system for transporting a person from a location of illness or injury to a medical facility comprising a stretcher in combination with at least one modularized medical care device, i.e. a medical care module. The medical care module particularly includes a modular housing and a medical care accessory arranged therein, such as an infusion pump, an oxygen supply device, a defibrillator, an electrocardiograph (EKG), an electroencephalograph (EEG), a fetal monitor, or a medical supply kit containing bandages, compresses, splints, antiseptics, IV solutions and equipment, drugs, syringes, and/or medical sharp instruments such as scissors, scalpels, trocars, and the like. The stretcher includes a frame and a patient support surface adapted to support the patient thereon. The stretcher further includes at least one module bay in which the medical care module can be received and carried, and/or at least one module carrier on which the medical care module can be mounted and carried. Particularly, the module bay is embodied as a receiving space below the patient support surface of the stretcher, in which a medical care module may be slidingly received. The module carrier is particularly embodied as a stacking carrier on which one or more medical care modules can be stacked and supported, for example on support bars or cross bars provided at the head end or foot end of the frame of the stretcher. Each medical care module has a standardized external configuration, i.e. a standardized shape and standardized dimensions, so that the several modules can be interchanged and received in any one of the module bays or on the module carrier.

With the inventive system it is especially advantageous that all of the necessary and important medical devices and medical supplies can be carried along directly in or directly on the stretcher. Thus, it is possible to provide an uninterrupted medical care or treatment of the patient continuously from the location at which the patient is first picked up, while carrying the patient on the stretcher into the ambulance or other vehicle, while transporting the patient in the vehicle, and then while carrying the patient from the vehicle to the final destination such as a medical facility. This can be carried out while continuously keeping the various devices connected to the patient, entirely without requiring additional attendants for carrying the various devices and without requiring the EMTs or other medical personnel to carry the devices or balance or otherwise support the devices on the top of the stretcher or on the body of the patient.

Once the patient has been brought to a hospital or other medical facility, the medical devices in the form of medical care modules can remain connected to the patient. When the patient is transferred to a hospital bed, the medical care modules can be transferred from the module bays provided in the stretcher to similarly configured module bays provided in a medical device cabinet that can be portably positioned next to the patient's hospital bed. Alternatively, the module carrier with the modules thereon can be removed from the stretcher and mounted directly on the side rail, headboard or footboard of the patient's hospital bed.

BRIEF DESCRIPTION OF THE DRAWINGS

In order that the invention may be clearly understood, it will now be described in connection with example embodiments, with reference to the accompanying drawings, wherein:

FIG. 1 is a schematic perspective view of a stretcher for carrying an ill or injured patient, according to a first embodiment of a system of the invention;

FIG. 2 is a schematic perspective view of the frame of the stretcher of FIG. 1, whereby the patient support surface has been removed in order to more clearly show features of the invention;

FIG. 3 is a detailed side view of a portion of the stretcher of FIG. 1, particularly showing a monitor display and input panel of the system according to the invention;

FIG. 4 is a schematic perspective view of a stretcher according to FIG. 1, further in combination with medical care modules received in module bays underneath the stretcher according to the invention;

FIG. 4A is a schematic perspective view of a representative medical care module comprising an oxygen supply device;

FIG. 4B is a schematic perspective view of another representative medical care module comprising a defibrillator;

FIG. 5 is a schematic side view of a medical device cabinet adapted to receive medical care modules therein;

FIG. 8 is a schematic perspective view of the module carrier with a plurality of medical care modules mounted thereon;

FIG. 9 is a schematic side view of the module carrier illustrating a mounting slot;

FIG. 10 is a schematic side view of an alternative embodiment of the module carrier including a mounting clamp rather than a mounting slot; and FIG. 11 is a schematic perspective view of a stretcher combining the embodiments of FIGS. 1 and 6.

Figure 6:
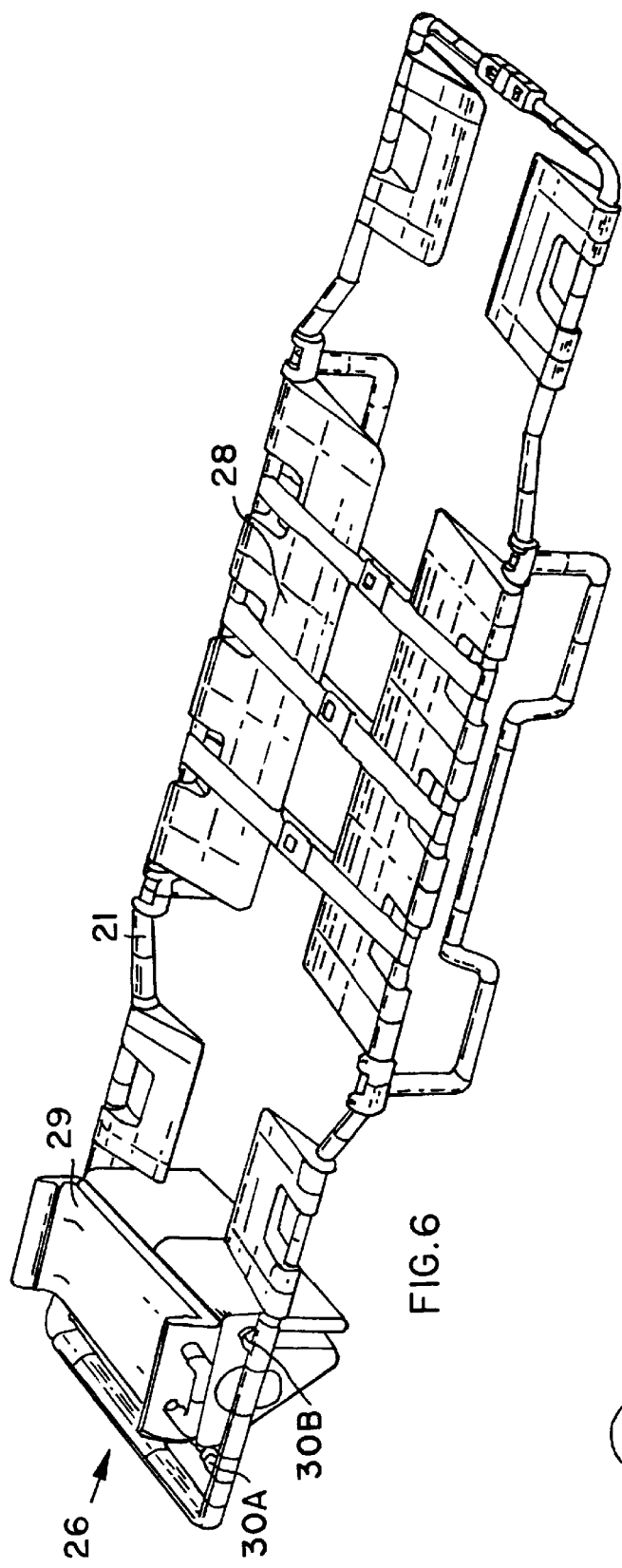
FIG. 6 is a schematic perspective view of a second embodiment of a stretcher for carrying a patient, in combination with a module carrier for carrying medical care modules thereon.

DETAILED DESCRIPTION OF PREFERRED EXAMPLE EMBODIMENTS AND OF THE BEST MODE OF THE INVENTION

FIG. 1 schematically shows a system for transporting a patient according to the invention, comprising a stretcher 1 that includes a frame 2 and a support surface 3 adapted to support the patient thereon. Bail-shaped stand legs 4 and 5 as well as carrying handles 6, 7, 8 and 9 are connected to and protrude from the stretcher frame 2. The legs 4 and 5 may be simple fixed legs, or may be pivotable between retracted and extended positions, or may be replaced by a collapsible undercarriage having wheels and the like. Generally, the legs 4 and 5 or other support for the stretcher 1 can be in accordance with any known configuration of such supporting structures for stretchers. The carrying handles 6, 7, 8 and 9 may be configured to slide telescopically into the frame 2 for a compact storage thereof, which makes the present stretcher 1 especially suitable for the typical tight space conditions that exist in many patient transport vehicles, such as ambulances, EMT vehicles, helicopters, or other aircraft. An alternative hand grip 6A for mounting on the carrying handles is shown in FIG. 2.

As especially shown in FIG. 2, support rails 13, 14, 15 and 16 are connected to and protrude downwardly from the frame 2 of the stretcher 1, preferably in the area between the legs 4 and 5. These support rails 13, 14, 15 and 16 extend crosswise or perpendicularly to the lengthwise axis of the stretcher frame 2, and respectively form module bays 10A, 11A and 12A therebetween. As shown in FIG. 1, the module bays 10A, 11A and 12A are each respectively adapted to receive a medical care module 10, 11 or 12 therein. The stand legs 4 and 5 of the stretcher 1 have a sufficient length or height to ensure that adequate space remains below the frame 2 of the stretcher 1 for accommodating the medical care modules 10, 11 and 12 when the stretcher 1 is placed down on the ground or other surface. Each medical care module 10, 11 and 12 comprises a modularized housing and a medical accessory arranged therein, such as an infusion pump, an oxygen supply device, a defibrillator, a fetal monitor, an EKG, an EEG, a medical supply kit containing any one or more of: bandages, splints, compresses, antiseptics, IV solutions and equipment, drugs, syringes, scissors, medical sharpware, and the like. If the respective medical care module comprises such a medical supply kit, then the housing thereof is essentially in the form of a drawer for storing the kit.

The details of the structure of the frame 2 and the support rails 13, 14, 15 and 16 can be seen in FIG. 2. The outermost support rails 13 and 16, i.e. the rails near the head end and the foot end of the stretcher 1 each respectively comprise a single slide rail 13A or 16A extending therefrom, while the middle support rails 14 and 15 each respectively have two slide rails 14A and 14B or 15A and 15B protruding laterally or substantially horizontally therefrom. The slide rails 13A, 14A, 14B, 15A, 15B, 16A are adapted to cooperate with corresponding or mating grooves provided along the sides of the housing of the respective medical care module 10, 11 and 12. Thus, the respective module 10, 11 or 12 can be slidingly pushed into the respective module bay 10A, 11A or 12A while slidingly engaging the respective slide rails in the manner of a drawer.

Depending on the particular medical device or equipment being embodied in the respective medical care module 10, 11 or 12, the module may be dimensioned to have a length substantially corresponding to the width of the stretcher 1, whereby the module can be termed a "full size module" that completely fills the space of the respective module bay 10A, 11A or 12A. Alternatively, the respective module 10, 11 or 12 can have a length corresponding to no more than half of the width of the stretcher 1, whereby the module may be termed a "half size module". Either type or size of module can be slidingly inserted into either of two open ends of each respective module bay 10A, 11A or 12A from either side of the stretcher 1, whereby two half size modules can be received from opposite sides in a single one of the module bays 10A, 11A or 12A. In any event, all of the modules have the same width corresponding to the spacing between the respective adjacent support rails 13, 14, 15 and 16, and all of the modules have the same slide groove configuration adapted to mate with the respective slide rails 13A, 14A, 14B, 15A, 15B, and 16A. Thus, all of the modules are fully interchangeable among any of the positions in the modular bays.

Many of the different types of medical care modules 10, 11 and 12 will typically have to be provided with electrical power. To achieve this, the medical care modules 10, 11 and 12 are provided with electrical contacts that complete an electrical connection with mating contacts provided in the module bays 10A, 11A and 12A. For example, electrical contacts can be provided on the sides of the modules 10, 11 and 12, which cooperate with mating contacts provided on the sides of the support rails 13, 14, 15 and 16. Particularly, the contacts can be provided in the slide grooves in the modules 10, 11 and 12, while the mating contacts are provides on the slide rails 13A, 14A, 14B, 15A, 15B, or 16A. As a further alternative, each module 10, 11 and 12 can include a plug-in contact that cooperates with a mating plug-in contact provided in the stretcher 1 when the respective module is pushed into its final position in the respective module bay.

The contacts provided on the stretcher 1 electrically connect the respective medical care modules 10, 11 and 12 to a power supply cable or the like provided in the stretcher 1, which in turn can be connected by an appropriate plug to the onboard power supply net of the transport vehicle such as an ambulance or aircraft. Moreover, while the stretcher 1 is being carried outside of the vehicle, a power supply is independently provided by a battery or the like in each respective medical care module 10, 11 or 12. As a further alternative, a battery pack can be embodied as a half size module or full size module that slides into one of the module bays 10A, 11A or 12A and thereby electrically connects to and provides power to the power supply cable or bus of the stretcher 1, which in turn distributes electrical power to all of the other modules 10, 11 and 12.

Additional contacts may be provided on the stretcher 1, for example on the support rails 13, 14, 15 and 16, for achieving a data transmission with the respective modules 10, 11 and 12. A monitor display 17 can be arranged at the head or foot end of the stretcher 1, and connected to the modules 10, 11 and 12 via appropriate conductors and the above mentioned data transfer contacts, so as to receive and display important medical data being provided by the medical care modules 10, 11 and 12. Moreover, the monitor display 17 can also incorporate an input panel, so that an EMT or other medical personnel who is carrying the stretcher 1 can simultaneously monitor the medical data being displayed on the display 17, monitor the functions of the various medical care modules 10, 11 and 12, and control the functions of the medical care modules 10, 11 and 12 via the input panel provided on the monitor display 17. It is also possible to operate each medical care module 10, 11 or 12 directly by means of input buttons or switches provided on a face panel of the respective module.

FIG. 3 shows the monitor display 17 by itself in detail. The display and input panel is tiltable about a tilting hinge 18. When the display and input panel 17 is tilted down into a substantially horizontal orientation parallel to and underneath the plane of the patient support surface of the stretcher, the panel 17 can be slidingly pushed into a box-like display panel storage bay 19. In this manner, when the display or input functions are not needed, the panel 17 can be stored in such a manner that it does not interfere with the care or treatment of the patient, and is also protected from damage or the like.

FIG. 4 is a perspective view of a stretcher 1 according to the first embodiment of the invention, equipped or outfitted with the medical care modules 10, 11 and 12 received in the module bays 10A, 11A and 12A underneath the stretcher 1. Since the separate medical care modules 10, 11 and 12 are fully interchangeable and exchangeable, it is possible to equip the stretcher 1 with the most important or most needed particular types of modules 10, 11 and 12, depending on and responsive to the particular illness or injury or accident situation to which an emergency response is being made. For example, if the emergency medical team is responding to a woman in labor, a fetal monitor module would be installed in a respective module bay. On the other hand, usually such a fetal monitor module can be omitted, to make room for more important modules for particular situations, such as a defibrillator module when responding to a cardiac arrest situation or an infuser pump module and a splint kit module when responding to an automobile accident or the like.

As an example, FIG. 4A shows a medical care module 20 embodied as an oxygen supply device with an oxygen mask 20A connected thereto, while FIG. 4B shows a medical care module 21 embodied as a defibrillator. These modules 20 and 21 are each provided with grooves 22 and 23 along the sides thereof, whereby the grooves 22 and 23 are configured so as to engage the above discussed slide rails in the module bays of the stretcher 1. The grooves 22 and 23 also include electrical contacts or contact rails so as to establish an electrical connection as well as a data transfer connection with the stretcher 1, as described above, when the respective module is inserted into the respective module bay.

Since the inventive system allows the most important medical devices and supplies needed for a given situation to be carried as respective modularized components directly under the stretcher 1, it is possible to provide an uninterrupted high level of medical care continuously from the time of picking up the patient, while carrying the patient on the stretcher 1 to the transport vehicle, while transporting the patient in the vehicle, and while carrying the patient on the stretcher from the vehicle to the medical facility or other end destination, without requiring an additional effort by the medical personnel for carrying the various different medical devices, and without requiring disconnection of the devices from the patient when the patient is transferred from one to the next phase of the transport.

Thus, the medical care being provided to the patient can continue in an uninterrupted fashion even when the patient is transferred from the stretcher 1 to a hospital bed or the like. As shown in FIG. 5, the inventive system further provides a medical device cabinet 25 that is embodied as a mobile unit and that is adapted to receive a plurality of the medical care modules in respective module bays of the mobile cabinet 25. For example, a medical care module 20 is slidingly received in a module bay 20A in a vertically stacked arrangement above other medical care modules. Thus, the various medical care modules that have already been connected to the patient (e.g. electrically in the case of an EKG module, or intravenously in the case of an infusion pump module) can remain connected to the patient as he or she is transferred from the stretcher 1 into a hospital bed. The various medical care modules are simply removed from their module bays in the stretcher 1 and transferred into the mobile medical device cabinet 25.

Just as in the case of the module bays in the stretcher 1, the module bays in the cabinet 25 can provide electrical power contacts and data transmission contacts, respectively for providing power to the individual modules and for receiving the data provided by the respective modules so as to monitor these data and the physical functions and conditions of the patient through a central monitoring unit that is also provided in the cabinet 25, for example. The central unit can also provide a central control of the functions of the several modules through corresponding contacts. The use of such a cabinet 25 in the system according to the invention further ensures that the medical care will be provided in an uninterrupted manner.

A second embodiment of a stretcher and an overall system according to the invention is shown in FIGS. 6 to 10. In this embodiment, the stretcher 26 essentially comprises a frame 27 and a patient support surface 28. Structural members such as crossbars or support bars 30A and 30B are connected to the head end or the foot end of the frame 27 for supporting a module carrier 29 thereon. The module carrier 29 is a separate unit that is removable from the stretcher 26. The module carrier 29 is adapted to receive and carry a plurality of medical care modules thereon. Since the module carrier 29 is removable from the stretcher 26, it can be manually carried by the medical personnel who are carrying the stretcher 26 or an accompanying attendant. This can be useful in situations in which the weight of the stretcher is to be reduced or the mobility of the stretcher is to be increased, or when the stretcher cannot be brought directly to the site of an injured or ill patient for administering immediate first aid, or when the present inventive system is to be retrofitted onto an existing conventional stretcher.

Figure 7:
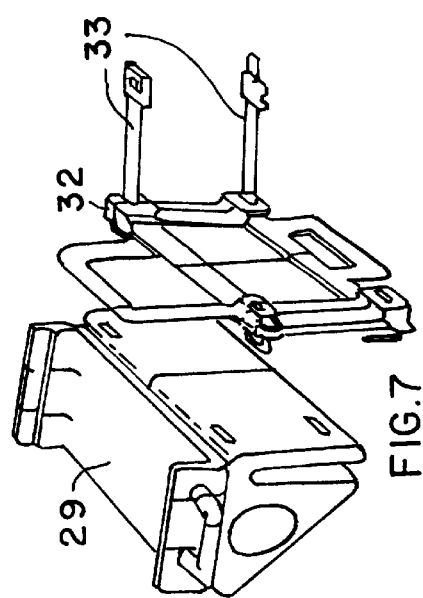
FIG. 7 is a schematic perspective view of the module carrier removed from the stretcher of FIG. 6, to be mounted on a backpack unit.
Figure 7B:
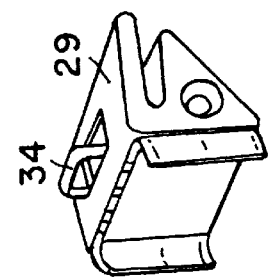
FIG. 7B shows an alternative embodiment for carrying the module carrier with a handle.
Figure 7A:
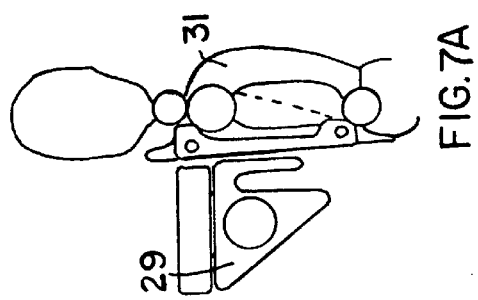
FIG. 7A shows the module carrier mounted on a backpack unit being carried by a person.

FIG. 7 shows a module carrier 29 adapted to be mounted on a backpack unit 32 equipped with carrying straps 33 such as shoulder straps, so that the module carrier 29 along with modules mounted in a stack thereon, can be carried in a backpack fashion on the back of a medical attendant 31 as shown in FIG. 7A. The module carrier 29 may be removably mounted or connected to the backpack unit 32 in any known fashion, such as by rotatable clasps or hooks or straps or the like. FIG. 7B shows an alternative possibility for carrying the module carrier 29. Namely, a handle 34 can be provided on the side of the module carrier 29, so that the module carrier 29 can be conveniently carried by hand, especially over short distances for example.

FIG. 8 shows the module carrier 29 in a perspective detail view, wherein the module carrier 29 comprises a support body 39 and a module mounting platform 37. The module mounting platform 37 is adapted to receive and engage a medical care module 36, for example by means of slide grooves along the side of the module engaging corresponding slide rails of the module mounting platform 37. The platform 37 is preferably rotatably arranged relative to the support body 39, so as to allow an optimal rotational adjustment of the medical care modules 35 and 36 to enable the best observation and operation of the displays and control switches provided on the face panels of the respective medical care modules.

The medical care modules 35 and 36 are each so configured so that several of the modules can be stacked and engaged with one another as shown in FIG. 8. For example, this can be achieved by engaging dovetail ribs or splines provided on the top of the 20 housing of module 36 with corresponding mating dovetail grooves provided on the bottom of the housing of module 35. Alternatively, this can be achieved by engaging heads of studs in respective keyhole slots or the like on the mating module. In general, any conventionally known manner of removably connecting together two modules can be used. Additionally, a strap or the like can secure the modules 35 and 36 to the module mounting platform 37. In order to conveniently carry the module carrier 29 with the medical care modules 35 and 36 mounted thereon, respective handles 38 are preferably provided on the sides of the module mounting platform 37.

A particular application in which the removable module carrier 29 is useful, is when a patient is to be transferred from the stretcher 26 into a hospital bed or the like, and the various medical devices connected to the patient are similarly to be transferred to the patient's bed. For this purpose, the support body 39 of the module carrier 29 serves to secure and hold the module mounting platform 37 onto the stretcher 26 and similarly onto the hospital bed or the like. For this reason, the support body 39 must be so dimensioned so that it can support several medical care modules such as the modules 35 and 36 with sufficient stability, while being modularly mountable on the stretcher 26 or on a hospital bed for example.

Moreover, the support body 39 is preferably configured large enough to accommodate a very important piece of medical equipment which is almost always necessary, such as an oxygen supply device 40 with an accompanying oxygen supply mask. For this purpose, it is advantageous to provide a sufficiently large housing for the support body 39 so that adequate storage space is provided within this housing to receive the oxygen supply device 40 and the oxygen mask.

Moreover, the support body 39 includes a mounting slot 41 that extends entirely across the width of the module carrier 29. Specifically, this mounting slot 41 has a U-shaped cross-section, to be easily mounted on the support crossbar 30B of the stretcher 27 in the first case, or to be mounted on the side rail or headboard or footboard 42 of a hospital bed in the second case.

FIG. 9 shows the mounting slot 41 of the support body 39 of the module carrier 29 mounted directly on a side rail 42 or the like of a hospital bed. The mounting slot 41 has a sufficient or vertical height to ensure that the module carrier 29 is stably and securely mounted on the side rail 42, whereby the weight of the module mounting platform 37 as well as the medical care module mounted thereon presses downward on the support body 39 and thereby exerts a bracing force against the side rail 42. Thus, the weight forces simultaneously ensure an adequate holding force for securely holding the entire module carrier on the bed. An additional securing of the module carrier on the bed rail 42 is not necessary. On the other hand, FIG. 10 shows an embodiment of the support body 39 of the module carrier 29 which has a U-sectional mounting channel 43 instead of the mounting slot 41. In order to achieve an adequately secure attachment or mounting of the module carrier 29 on the bed rail 42, an additional clamping element 44 cooperates with the mounting channel 43 to clamp the bed rail 42 therein.

FIG. 11 shows a system including a stretcher 1 that combines the features of the first and second embodiments discussed above.

Namely, the stretcher 1 is equipped with medical care modules 10, 11 and 12 received in corresponding module bays below the stretcher frame 2, as well as a module carrier 29 arranged at the head or foot end of the stretcher 1 for receiving additional medical care modules thereon.

Although the invention has been described with reference to specific example embodiments, it will be appreciated that it is intended to cover all modifications and equivalents within the scope of the appended claims. It should also be understood that the present disclosure includes all possible combinations of any individual features recited in any of the appended claims.

What is claimed is:

1. A system for continuously providing medical care to a patient who needs to be transported, said system comprising a portable module carrier that is for carrying a medical care module thereon and that comprises:
    a support base body adapted to be removably mounted on a stretcher or a hospital bed;
    a module mount platform connected to said support base body and adapted to have a medical care module removably mounted thereon; and a carrying unit onto which said support base body is removably mounted to facilitate carrying of said module carrier by a person, wherein said carrying unit comprises a backpack member on which said support base body is removably mounted, and shoulder straps extending from said backpack member and adapted to be worn on the shoulders of a person who may carry said module carrier on the person's back;

wherein said module carrier is so configured and arranged so that the medical care module remains accessible and functional for use while said module carrier is being carried on the person's back.

2. The system according to claim 1, wherein said portable module carrier further comprises a carrying handle connected to said support base body to facilitate carrying of said module carrier by hand by a person.

3. The system according to claim 1, wherein said support base body has at least one space therein, and further comprising an oxygen supply device and an oxygen mask received in said at least one space.

4. The system according to claim 1, wherein said module mount platform is rotatably connected to said support base body and is rotatable relative thereto.

5. The system according to claim 1, wherein said support base body has a mounting slot therein having a vertical slot height extending through a majority of a height of said support base body and a slot length extending entirely through a width of said support base body, and wherein said mounting slot is adapted to be removably mounted on a support bar of a frame of the stretcher or on a rail of the hospital bed.

6. The system according to claim 1, wherein said support base body includes a mounting channel and a movable clamp member clampingly cooperating with said channel.

7. The system according to claim 1, further comprising a medical care module that is removably mounted on said module mount platform, and that comprises a standardized modular housing and at least one medical care accessory arranged in said housing.

8. The system according to claim 7, wherein said modular housing is so configured that it can be received in a module receiving bay provided in a stretcher.

9. The system according to claim 8, wherein opposite side walls of said modular housing have grooves therein adapted to slidingly engage slide rails provided in a module receiving bay in a stretcher.

10. The system according to claim 9, wherein said modular housing further comprises electrical contacts provided in said grooves.

11. The system according to claim 7, further comprising a medical device storage cabinet that comprises a cabinet body with a plurality of module receiving bays adapted to respectively removably receive said medical care module therein.

12. The system according to claim 7, further comprising a stretcher comprising a frame and a patient support surface that is supported by said frame and that is adapted to support said patient thereon;

wherein said at least one medical care accessory is adapted to be used for a medical assessment, stabilization or treatment of said patient; and wherein said support base body of said module carrier is adapted to be mounted on said frame of said stretcher at at least one of a head end and a foot end of said stretcher.

13. The system according to claim 12, wherein said medical care accessory is selected from the group consisting of an infusion pump, an oxygen supply device, a defibrillator, an electrocardiograph, an electroencephalograph, a fetal monitor, and a medical supply kit including at least one of a bandage, a compress, a splint, an antiseptic, an intravenous solution, a drug, a hypodermic syringe, and a medical sharp instrument.

14. The system according to claim 12, wherein said frame of said stretcher includes at least one support bar, and said support base body of said module carrier is removably mountable on said support bar.

15. The system according to claim 12, wherein said stretcher has at least one module receiving bay arranged in connection with said frame below said patient support surface; and wherein said module receiving bay and said medical care module are respectively configured so that said medical care module can be received and supported in said module receiving bay.

16. The system according to claim 15, wherein said medical care module is removable so that it can be selectively inserted into said module receiving bay and selectively removed from said module receiving bay.

17. The system according to claim 15, comprising a first plurality of said medical care modules respectively comprising different ones of said medical care accessories, wherein said standardized modular housing of each respective one of said medical care modules has a same first standardized configuration so that any one of said medical care modules can be selectively inserted into said module receiving bay.

18. The system according to claim 17, comprising a plurality of said stretchers, wherein any one of said medical care modules can be selectively inserted into said module receiving bay of any one of said stretchers.

19. The system according to claim 17, wherein said stretcher includes a plurality of said module receiving bays arranged side-by-side adjacent one another along a lengthwise axis of said stretcher, and wherein each one of said bays respectively has an opening along a first long side of said stretcher through which a respective one of said medical care modules can be inserted into and removed from said respective bay.

20. The system according to claim 19, wherein each one of said bays further respectively has a second opening through which a respective one of said medical care modules can be inserted into and removed from said respective bay along a second long side of said stretcher opposite said first long side.

21. The system according to claim 19, wherein said first standardized configuration is a full-size module configuration having a standard module width that substantially corresponds to a bay width of said module receiving bays along said lengthwise axis of said stretcher, and having a full-size depth perpendicular to said module width that substantially corresponds to a stretcher width of said stretcher perpendicular to said lengthwise axis.

22. The system according to claim 21, further comprising a second plurality of said medical care modules, wherein said standardized modular housing of each respective one of said modules of said second plurality has a same second standardized configuration, which is a half-size configuration with a width corresponding to said standard module width and a depth corresponding to no more than half of said full-size depth.

23. The system according to claim 19, further comprising a battery pack module including a respective one of said standardized module housings, and a battery arranged in said housing, as well as electrical contacts adapted to connect said battery pack module to at least one of said medical care modules.

24. The system according to claim 15, wherein said module receiving bay comprises support rails that are connected to said frame and that are spaced apart from each other with a space therebetween for receiving said medical care module in said space supported on said support rails.

25. The system according to claim 24, further comprising first electrical contacts provided on at least one of said support rails, and second electrical contacts arranged on said medical care module and adapted to respectively establish electrical connections with said first electrical contacts when said medical care module is received in said module receiving bay.

26. The system according to claim 25, wherein said first electrical contacts include first power supply contacts and first data transmission contacts, and said second electrical contacts comprise second power supply contacts and second data transmission contacts.

27. The system according to claim 25, further comprising a monitor display mechanically connected to said frame of said stretcher and electrically connected to said medical care module via said first and second electrical contacts.

28. The system according to claim 27, further comprising an input panel combined with said monitor display.

29. The system according to claim 27, further comprising a monitor storage bay incorporated in said stretcher, wherein said monitor is tiltably and slidably arranged relative to said frame of said stretcher so as to be selectively deployable from and storable in said monitor storage bay.

30. The system according to claim 7, comprising a plurality of said medical care modules that are each adapted to be removably connected directly to another one of said medical care modules.

* * * * *